United States Patent
Jania et al.

(10) Patent No.: US 11,364,121 B2
(45) Date of Patent: Jun. 21, 2022

(54) ENGINEERED BONE GRAFT IMPLANT AND METHODS OF USING THE SAME

(71) Applicant: Vertical Spine LLC, Wall, NJ (US)

(72) Inventors: Eric Robert Jania, Califon, NJ (US); Thomas Aloysius Crowley, Spring Lake, NJ (US); James Joseph Yue, Guilford, CT (US); Frank P. Cammisa, Jr., Greenwich, CT (US)

(73) Assignee: Vertical Spine LLC, Wall, NJ (US)

( * ) Notice: Subject to any disclaimer, the term of this patent is extended or adjusted under 35 U.S.C. 154(b) by 5 days.

(21) Appl. No.: 16/489,283

(22) PCT Filed: Feb. 27, 2018

(86) PCT No.: PCT/US2018/020019
§ 371 (c)(1),
(2) Date: Aug. 27, 2019

(87) PCT Pub. No.: WO2018/157156
PCT Pub. Date: Aug. 30, 2018

(65) Prior Publication Data
US 2020/0113697 A1    Apr. 16, 2020

Related U.S. Application Data

(60) Provisional application No. 62/464,054, filed on Feb. 27, 2017.

(51) Int. Cl.
*A61F 2/28* (2006.01)
*A61L 27/36* (2006.01)
*A61F 2/30* (2006.01)

(52) U.S. Cl.
CPC .......... *A61F 2/2846* (2013.01); *A61L 27/365* (2013.01); *A61F 2002/2835* (2013.01); *A61F 2002/3082* (2013.01); *A61F 2002/30224* (2013.01); *A61F 2002/30622* (2013.01); *A61F 2310/00179* (2013.01); *A61F 2310/00988* (2013.01); *A61L 2300/414* (2013.01)

(58) Field of Classification Search
CPC ............ A61F 2/2846; A61F 2002/2835; A61F 2002/30622; A61F 2/28; A61F 2002/3082; A61F 2002/30224
See application file for complete search history.

(56) References Cited

U.S. PATENT DOCUMENTS

| | | | |
|---|---|---|---|
| 5,275,611 A | 1/1994 | Behl | |
| 5,972,368 A | 10/1999 | McKay | |
| 6,102,948 A | 8/2000 | Brosnahan, III | |
| 6,200,347 B1 * | 3/2001 | Anderson | A61F 2/28 623/16.11 |
| 6,368,298 B1 | 4/2002 | Beretta et al. | |
| 6,979,307 B2 | 12/2005 | Beretta et al. | |
| 7,745,106 B2 | 6/2010 | Beretta et al. | |
| 8,802,362 B2 | 8/2014 | Grippi et al. | |

(Continued)

OTHER PUBLICATIONS

International Search Report and Written Opinion dated May 1, 2018, for related International Application No. PCT/US2018/020019, 7 pages.

*Primary Examiner* — Javier G Blanco
(74) *Attorney, Agent, or Firm* — Morgan, Lewis & Bockius LLP (57) ABSTRACT

A bone graft implant and methods of using the same are provided herein.

51 Claims, 3 Drawing Sheets

(56) References Cited

U.S. PATENT DOCUMENTS

| | | |
|---|---|---|
| 10,667,841 B2 | 6/2020 | Yue |
| 2003/0009235 A1 | 1/2003 | Manrique et al. |
| 2003/0065333 A1 | 4/2003 | DeMayo |
| 2003/0078660 A1 | 4/2003 | Clifford et al. |
| 2003/0225459 A1 | 12/2003 | Hammer et al. |
| 2004/0210311 A1 | 10/2004 | Lange et al. |
| 2005/0033425 A1* | 2/2005 | Schwab ............... A61F 2/4465 623/16.11 |
| 2005/0273165 A1 | 12/2005 | Griffiths et al. |
| 2007/0055254 A1* | 3/2007 | Ihde ..................... A61C 8/001 606/71 |
| 2008/0234687 A1* | 9/2008 | Schaller ................. A61F 2/44 606/90 |
| 2008/0234827 A1 | 9/2008 | Schaller et al. |
| 2010/0256777 A1* | 10/2010 | Datta .................... A61L 27/18 623/23.72 |
| 2010/0330533 A1* | 12/2010 | Cottrell ................ A61C 8/005 433/174 |
| 2011/0054408 A1 | 3/2011 | Wei et al. |
| 2012/0296441 A1 | 11/2012 | Mikhail et al. |
| 2013/0096681 A1 | 4/2013 | Ray, III et al. |
| 2013/0289629 A1 | 10/2013 | Miller |
| 2014/0199657 A1 | 7/2014 | Moon et al. |
| 2014/0277139 A1 | 9/2014 | Vrionis et al. |
| 2017/0151061 A1* | 6/2017 | Lavi ..................... A61F 2/4225 |
| 2017/0340455 A1 | 11/2017 | Greter et al. |
| 2018/0140327 A1 | 5/2018 | Yue |
| 2018/0214192 A1 | 8/2018 | Roby et al. |

* cited by examiner

ENGINEERED BONE GRAFT IMPLANT AND METHODS OF USING THE SAME

CROSS-REFERENCE TO RELATED APPLICATIONS

This application is a U.S. National Stage application of International Application No. PCT/US2018/020019, filed Feb. 27, 2018, which claims the benefit of priority to U.S. Provisional Application No. 62/464,054 filed Feb. 27, 2017, the entireties of which are incorporated herein by reference.

FIELD OF THE INVENTION

The invention described herein relates generally to an implant and more particularly, but not exclusively, to a bone graft implant and methods of using the same.

BACKGROUND OF THE INVENTION

A need exists in the field for bone implant solutions that may be used with minimally invasive surgery (MIS).

The invention meets the needs in the field by providing a bone implant solution that may be used in MIS procedures.

SUMMARY OF THE INVENTION

In an embodiment, the invention includes a bone graft implant. In some embodiments, the bone graft implant may include a bioincorporable bone graft implant configured to be connected or otherwise affixed to bone and incorporated into a patient's tissues. In some embodiments, the bone graft implant of the invention, or portions thereof, may be biocompatible, bioabsorbable, and/or bioresorbable. In some embodiments, the bone graft implant may be a construct or tissue scaffold.

In some embodiments, the bone graft implant of the invention may include a first portion and a second portion. In some embodiments, the first and/or second portions of the bone graft implant may be porous. In some embodiments, the pores of the first and second portion may include open cell portions, closed cell portions, or a combination thereof.

In some embodiments, at least one of the first portion and second portion of the bone graft implant may include one or more reliefs or cut outs that may be configured to allow the bone graft implant to be flexed or manipulated to ease introduction into a patient to be treated when applied to a patient's bone.

In some embodiments, the second portion of the bone graft implant may be configured to be placed proximate to a bone surface. In some embodiments, the bone surface may be cancellous bone.

In some embodiments, the bone graft implant may include a bioincorporable membrane or matrix that may be disposed about the first and/or second portion of the bone graft implant.

In some embodiments, the bone graft implants may be made from allograft, autograft, xenograft, cortical, cancellous, cartilage, and combinations of, synthetic HA, B-TCP, Ceramic, PLA, PLGA, PLLA or other such materials and may be incorporated with growth factors, plasma (e.g., platelet rich plasma), platelets (e.g., intact platelets), cells, peptides or other such materials.

In some embodiments, the bone graft implants may have an outer diameter ranging from about 3.5 mm to about 9.45 mm and a length ranging from about 20 mm to about 120 mm. In some embodiments, the bone graft implants may be a single piece of material, multiple links of material, or a composite material.

In some embodiments, the bone graft implants are cylinders, rectangular, trapezoidal, flat, convex, concave, and may have a channel on one or both sides for easy placement against a patient's bone or for buttressing against a bone, a metal rod, or a PEEK rod attached thereto or held in place to pedicle screws.

In some embodiments, the bone graft implants may be trimmed to size and snapped onto a rod by press fit or by means of sutures.

In some embodiments, the bone graft implants described herein may be flexible, moldable, and may be axially and/or radially conformable, by removing the mineral content through demineralization processes, or by creating V- or U-shaped reliefs placed on alternating sides or by changing the porosity at specific sections or throughout an entire implant, or through being pre-hydrated with a fluid, such as saline, water, alcohol, or other biocompatible fluids.

In some embodiments, the bone graft implants have different porosities throughout the implant or different porosities on the top and bottom, lengthwise, to wick up fluid, blood, bone marrow, marrow concentrate, plasma (e.g., platelet rich plasma), growth factors, cells, peptides, or other such materials.

In some embodiments, the bone graft implants are cannulated for delivery down, on, or through a guide wire or k-wire.

In some embodiments, the bone graft implants have axial or radial holes to accommodate the fixation of biologic platelet rich fibrin membrane, platelet rich fibrin matrix, amnion, chorion, dermis, or fascia, from autograft, allograft or xenograft, or synthetic materials impregnated with growth factors, plasma (e.g., platelet rich plasma), cells, peptides, or other such materials.

In some embodiments, the bone graft implants have a collar that is concave or have an annulus at both ends at a smaller diameter than the body of the implant.

In some embodiments, the bone graft implants have clamp shaped ends or concave ends to secure the implants to a screw or washer to limit movement of the implant.

In an embodiment, the invention may include a method for treating bone in a patient in need thereof. In some embodiments, the method may include a method for fusing one or more vertebrae of a patient in need of such treatment. In some embodiments, the method may include introducing a bone graft implant as described herein to a surface of the patient's bone and affixing the bone graft implant to said surface of the patient's bone. In some embodiments, the method may include affixing the bone graft implant such that the second portion of the bone graft implant is placed proximate to the surface of the patient's bone. In some embodiments, the first portion of the bone graft implant may be placed such that the first portion of the bone graft implant may contact the surface of the patient's bone.

In an embodiment, the invention may include a kit comprising a bone graft implant as described herein. In some embodiments, the kit may include an introducing device or introducing system configured to introduce the bone graft implant at a surface of the patient's bone. In some embodiments, the kit may include one or more fixation elements configured to affix the bone graft implant to the surface of the patient's bone.

In an embodiment, the invention may include a method of preparing a bone graft implant as described herein. In some embodiments the method may include modifying the porosity of the bone graft implant by demineralizing the bone graft implant. In some embodiments, the method may include modifying the porosity of the bone graft implant by demineralizing at least one of the first and second portions of the bone graft implant. In some embodiments, the method may include selectively demineralizing the first portion of the bone graft implant such that the first portion has greater porosity or is otherwise more porous than that the first portion. In some embodiments, demineralizing the first and/or second portion of the bone graft device may include a step of providing a porous gradient such that pore sizes of the first portion and/or section portion increase or decrease along the axis or length of the bone graft implant.

BRIEF DESCRIPTION OF THE DRAWINGS

The foregoing summary and the following detailed description of the exemplary embodiments of the invention may be further understood when read in conjunction with the appended drawings, in which.

DETAILED DESCRIPTION OF THE INVENTION

Figure 1A:
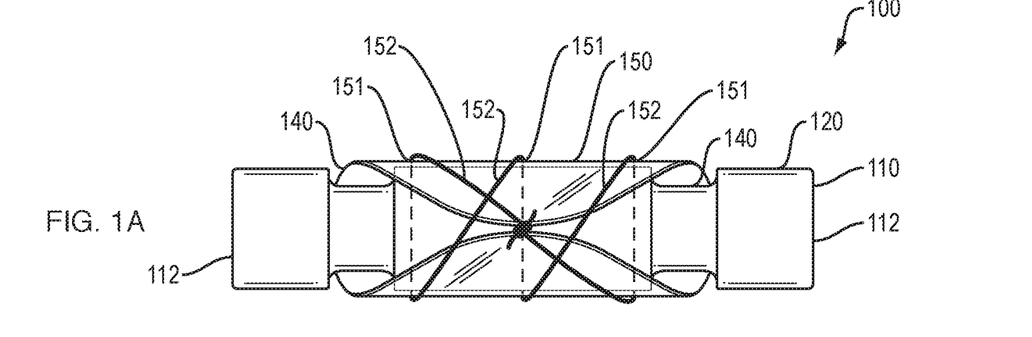
FIGS. 1A to 1C illustrate a bone graft implant embodiment of the invention that includes two U-shaped reliefs about the cylindrical body in a top-down view (FIG. 1A), a side-on view (FIG. 1B), and a perspective side-on view (FIG. 1C).
Figure 1B:
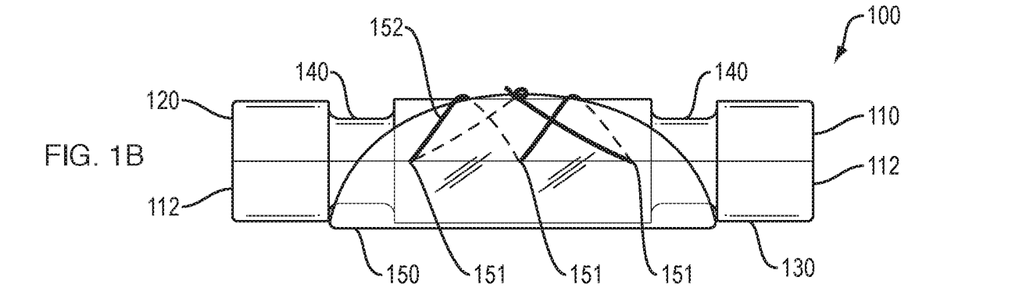
Figure 1C:
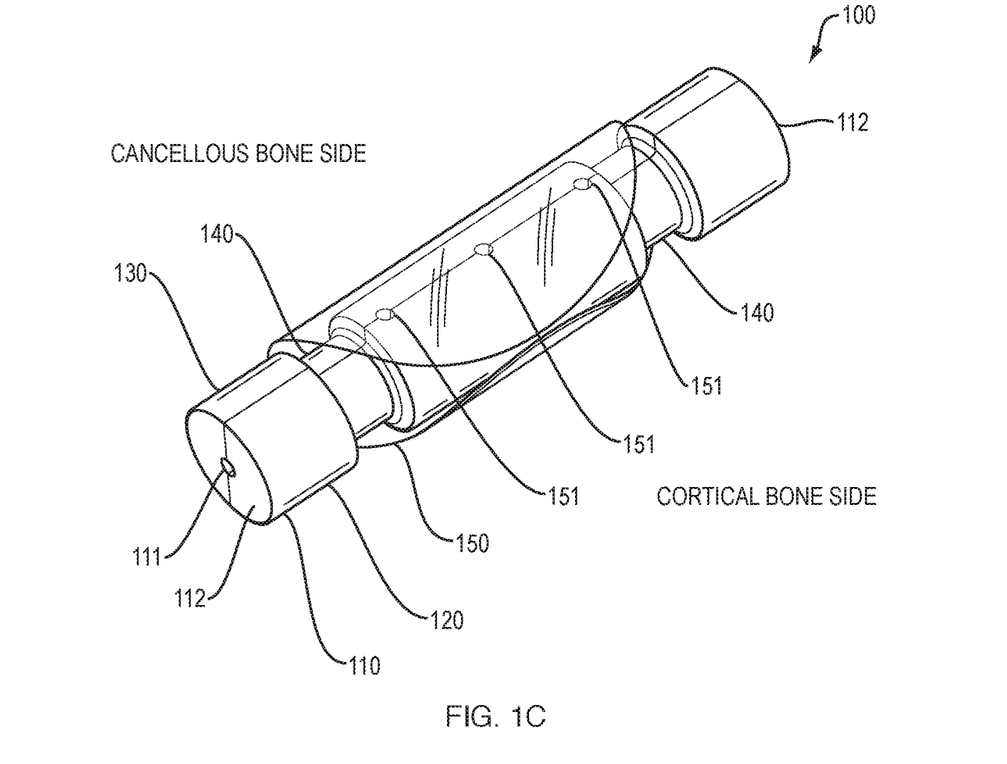

Referring now to the figures, wherein like elements are numbered alike throughout, FIGS. 1A to 1C describe a bone graft implant of the invention 100 that includes two U-shaped reliefs 140 and is generally cylindrical. The bone graft implant 100 may include a body 110 having a first portion 120 and a second portion 130, where the second portion 130 may be configured for placement proximate to a bone surface in a patient. The body 110 may further include a cannula 111 that may extend from one end 112 to another end 112 of the body 110. In some embodiments, the bone graft implant 100 may include a bioincorporable membrane or matrix 150 that may be affixed to the body 110 with membrane fixation element or elements 152 that are connected to the body 110 through radial holes 151.

As used herein, the term "bioincorporable" as applied to any materials or components refers to any such materials or components that may be incorporated into a tissue and thereby become substantially indistinguishable from the tissue.

In some embodiments, the bone graft implant 100 may include bioabsorbable and/or biodegradable materials. As used herein, the terms "biodegradable", "biodegradation", "degradable", "degradation", "degraded", "bioerodible", "erodible" or "erosion" are used interchangeably and are understood as the breaking down or the susceptibility of a material or component to break down or be broken into products, byproducts, components or subcomponents over time such as days, weeks, months or years. As used herein, the terms "bioabsorbable", "absorbable", "resorbable" and "bioresorbable" are used interchangeably and are defined as the biologic elimination of any materials or components through metabolic degradation and/or excretion.

In some embodiments, the bone graft implant 100 may include body 110 that may have a circular cross-section, square or rectangular cross-section, or trapezoidal cross section. In some embodiments, body 110 includes a circular cross-section and is cylindrical. Alternatively, the body 110, or a segment or portion thereof, may be flat, convex, or concave. In some embodiments, the body 110 may have an outer diameter of about 3 mm to about 10 mm, or about 3.5 mm to about 9.5 mm. In some embodiments, the cannula 111 may have a diameter of about 0.5 mm to about 3.0 mm, or about 1 mm to about 2.5 mm. In some embodiments, the body 110 may have a length, along the axis of the body 110, of about 15 mm to about 125 mm, or about 20 mm to about 120 mm, or about 25 mm to about 115 mm, or about 30 mm to about 110 mm, or about 35 mm to about 105 mm, or about 40 mm to about 100 mm, or about 45 mm to about 95 mm, or about 50 mm to about 90 mm, or about 55 mm to about 85 mm, or about 60 mm to about 80 mm. In some embodiments, the body 110 may have a length of greater than about 20 mm, or greater than about 25 mm, or greater than about 30 mm, or greater than about 35 mm, or greater than about 40 mm, or greater than about 45 mm, or greater than about 50 mm, or greater than about 55 mm, or greater than about 60 mm, or greater than about 65 mm, or greater than about 65 mm, or greater than about 70 mm, or greater than about 75 mm, or greater than about 80 mm, or greater than about 85 mm, or greater than about 90 mm, or greater than about 95 mm, or greater than about 100 mm, or greater than about 105 mm, or greater than about 110 mm, or greater than about 115 mm, or greater than about 120 mm.

In some embodiments, the graft body 110 may include a first portion 120 and a second portion 130. The first and second portions 120 and 130 may be composed of autograft cortical bone, autograft cancellous bone, autograft cartilage, or a combination thereof. In some embodiments, the first and second portions 120 and 130 may be composed of allograft cortical bone, allograft cancellous bone, allograft cartilage, or a combination thereof. In some embodiments, the first and second portions 120 and 130 may be composed of xenograft cortical bone, xenograft cancellous bone, xenograft cartilage, or a combination thereof. In some embodiments, the first and second portions 120 and 130 may be composed of synthetic cortical bone, synthetic cancellous bone, synthetic cartilage, or a combination thereof. In some embodiments, the first and second portions 120 and 130 may include one or more of hyaluronic acid, B-TCP, ceramic, PLA, PLGA, and PLLA. In some embodiments, the first and second portions 120 and 130 may be hydrated and/or pre-hydrated with a fluid such as saline, water, alcohol, or other biocompatible fluid.

In some embodiments, the first portion and second portion 120 and 130 may include a composite of one or more materials. Alternatively, the first and second portion 120 and 130 may be uniform.

In some embodiments, the first portion 120 or second portion 130 may include a channel that may be configured to abut or receive a portion of bone or metal rods/screws or PEEK rods/screws.

In some embodiments, the first and second portions 120 and 130 may include growth factors, plasma (e.g., platelet rich plasma), platelets (e.g., intact platelets), cells, peptides, or a combination thereof.

In some embodiments, the first and second portions 120 and 130 may be porous and may include an open-cell pore structure and/or a closed-cell pore structure. In some embodiments, the first portion 120 may have a pore size that is greater than the pore size of the second portion 130. In some embodiments, the first portion 120 may have a pore size that is smaller than the pore size of the second portion 130. In some embodiments, the first portion 120 and the second portion 130 may have about the same porosity or pore size. In some embodiments, the pores of the first portion 120 and/or the second portion 130 may have uniform pore sizes. In some embodiments, the pores of the first portion 120 and/or the second portion 130 may have non-uniform pore sizes.

In some embodiments, the portions of the body 110 may include a porous gradient where the pore size at a surface of the portion is greater than the pore size at the interior of the portion. In some embodiments, the portions of the body 110 may include a porous gradient wherein the pore size at a surface of the portion is less than the pore size at the interior of the portion. In some embodiments, the portions of the body 110 may include a porous gradient where the pore size at a surface of the portion is greater than the pore size at a second surface of the portion. In some embodiments, the portions of the body 110 may include pore sizes that vary lengthwise along the axis of the body 110.

The reliefs 140 allow the bone graft to flex upon introduction to a patient's bone. In addition, the reliefs 140 may allow the bone graft implant to be conformable and/or moldable to an irregularly shaped bone surface. In some embodiments, the reliefs 140 may include a plurality of reliefs. In some embodiments, the reliefs 140 may include scalloped reliefs, V-shaped reliefs, and/or U-shaped reliefs. FIGS. 1A to 1C demonstrate reliefs 140 that are U-shaped.

In some embodiments, the bone graft implant 100 includes a bioincorporable membrane or matrix 150. In some embodiments, the bioincorporable membrane 150 may include a fibrin membrane or matrix. In some embodiments, the bioincorporable membrane 150 may include a platelet rich fibrin membrane. In some embodiments, the bioincorporable membrane 150 may include one or more of autograft amnion, autograft chorion, autograft dermis, autograft fascia, or a combination thereof. In some embodiments, the bioincorporable membrane 150 may include one or more of allograft amnion, allograft chorion, allograft dermis, allograft fascia, or a combination thereof. In some embodiments, the bioincorporable membrane 150 may be a platelet rich fibrin membrane or matrix. In some embodiments, the bioincorporable membrane 150 may include growth factors, plasma (e.g., platelet rich plasma), cells, peptides, or a combination thereof.

In some embodiments, the bioincorporable membrane 150 may be secured to the body 110 with one or more membrane fixation elements 152. The membrane fixation elements 152 may communicate with the body 110 through one or more securing holes 151 that may radially traverse the width of the body 110. In some embodiments, the membrane fixation elements 152 may include sutures, screws, adhesive, or a combination thereof. In certain embodiments, the fixation element 152 may include sutures that are interwoven between the bioincorporable membrane 150 and the body 110.

In some embodiments, the bioincorporable membrane 150 may be FIBRINET®. In some embodiments, the bioincorporable membrane 150 may include a fibrin web, matrix, or membrane as described and prepared in one or more of U.S. Pat. Nos. 6,368,298, 6,979,307, 7,745,106, and 8,802,362, the entirety of which are incorporated herein by reference.

In some embodiments, the bioincorporable membrane 150 includes, or may be implanted with, one or more of an antibiotic, an antimicrobial, an antibiofilm, an analgesic, a cancer therapeutic, a platelet-growth factor, bone morphogenic protein cells for gene therapy, stem cells for additional uses, and other hormones. Other therapeutic agents which can be administered may also be included. Examples of antibiotics include, but are not limited to, ampicillin, erythromycin and tobramycin. Antimicrobials include, but are not limited to silver. Antibiofilms include, but are not limited to salicylic acid. Analgesics include, but are not limited to, aspirin and codeine. Cancer therapeutics include, but are not limited to, 5-fluoro-uracil.

Accordingly, in some embodiments of the invention, the bone graft implant 100 may act as a delivery vessel, or mechanical delivery device, for delivering the bioincorporable membrane 150, as described herein, to selected tissues of the body which may include, without limitation, bone tissue. For example, the bioincorporable membrane 150 may include, or have deposited thereon, an antibiotic, an antimicrobial, an antibiofilm, an analgesic, a cancer therapeutic, a platelet-growth factor, bone morphogenic protein cells, or stem cells for the treatment of diseases that require such delivery.

In certain embodiments, one or more of the ends 112 of the body 110 may include a portion that may receive a bone fixation element that may be provided to affix the bone graft implant 100 to a portion of a patient's bone. In some embodiments, the bone fixation element may include bone, metal rods/screws, or PEEK rods/screws (e.g., bone screws with associated washers), sutures, staples, adhesive, or a combination thereof.

In some embodiments, the ends 112 may include a concave collar at one or both ends 112 of the bone graft implant 100. In some embodiments, the ends 112 may include an annulus having a diameter that is less than or smaller than the diameter of the body 110 of the bone graft implant 100. In some embodiments, one or both ends 112 of the body 110 may have a convex shape or concave shape. In some embodiments, one or both ends 112 of the body 110 may be clamp shaped.

Figure 2A:
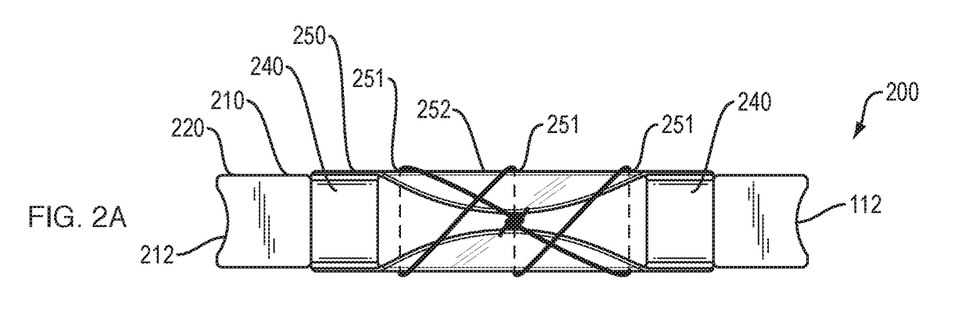
FIGS. 2A to 2C illustrate a bone graft implant embodiment of the invention that includes two U-shaped reliefs about the square-tubular body in a top-down view (FIG. 2A), a side-on view (FIG. 2B), and a perspective side-on view (FIG. 2C).
Figure 2B:
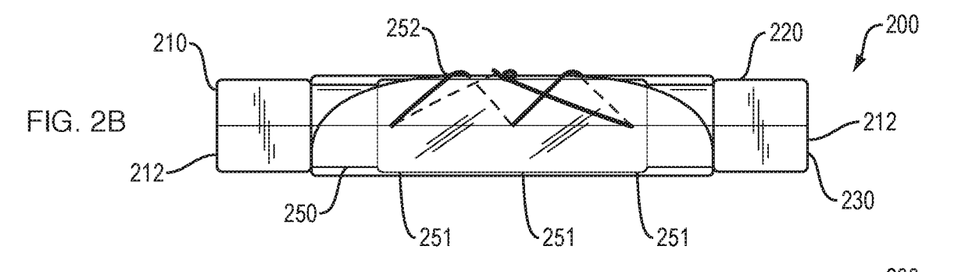
Figure 2C:
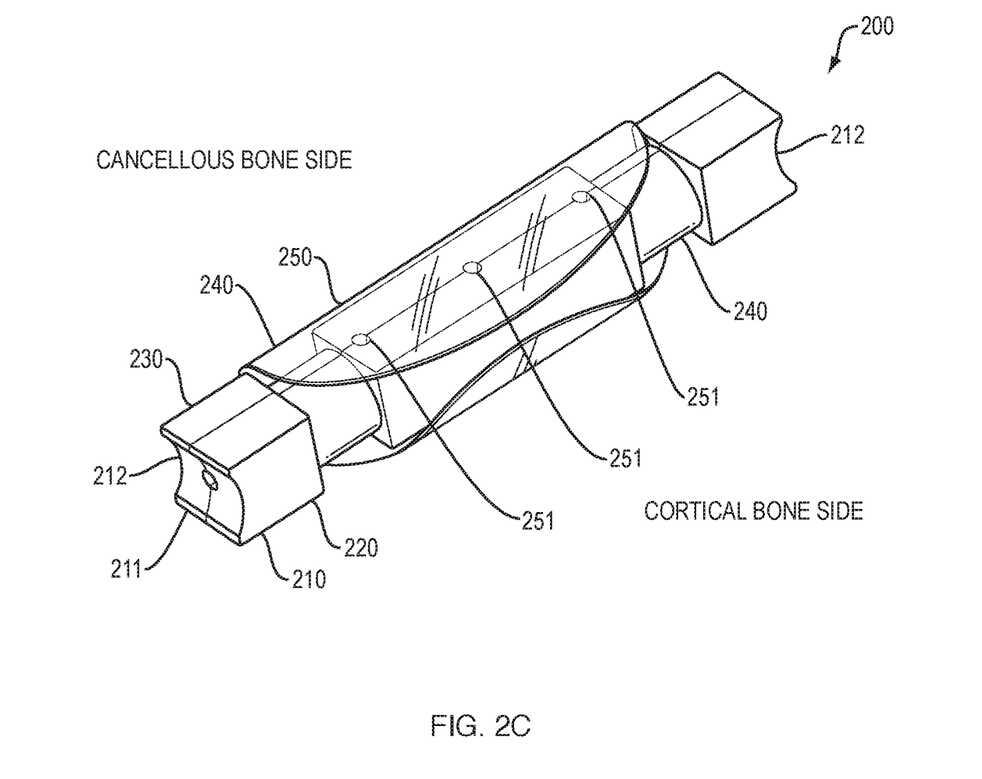

As shown in FIGS. 2A to 2C, some embodiments of the invention includes a bone graft implant 200. The bone graft implant 200 includes a body 210 having a generally square cross section, but with U-Shaped reliefs 240. The body 210 includes first portion 220 and second portion 230. Furthermore, the body 210 includes a cannula 211 that traverses the length of body 210 from end 212 to the other end 212. The ends 212 are configured to be concave as shown in FIGS. 2A and 2C. In some embodiments, the bone graft implant 200 may include a bioincorporable membrane or matrix 250 that may be affixed to the body 210 with membrane fixation elements 252 that are connected to the body 210 through radial holes 251. As shown in FIGS. 2A and 2B, the membrane fixation element 252 may be sutures.

Figure 3A:
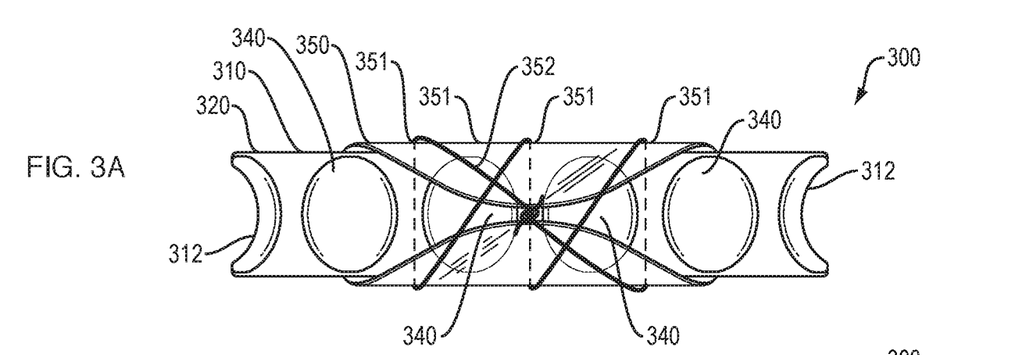
FIGS. 3A to 3C illustrate a bone graft implant embodiment of the invention that includes a plurality of scalloped reliefs (or v-shaped) reliefs on cortical bone side facing (first portion) and cancellous bone side facing (second portion) of the cylindrical body in a top-down view (FIG. 3A), a side-on view (FIG. 3B), and a perspective side-on view (FIG. 3C).
Figure 3B:
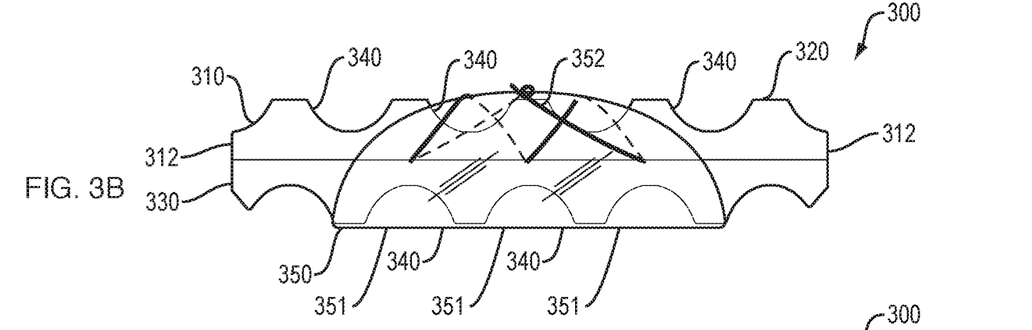
Figure 3C:
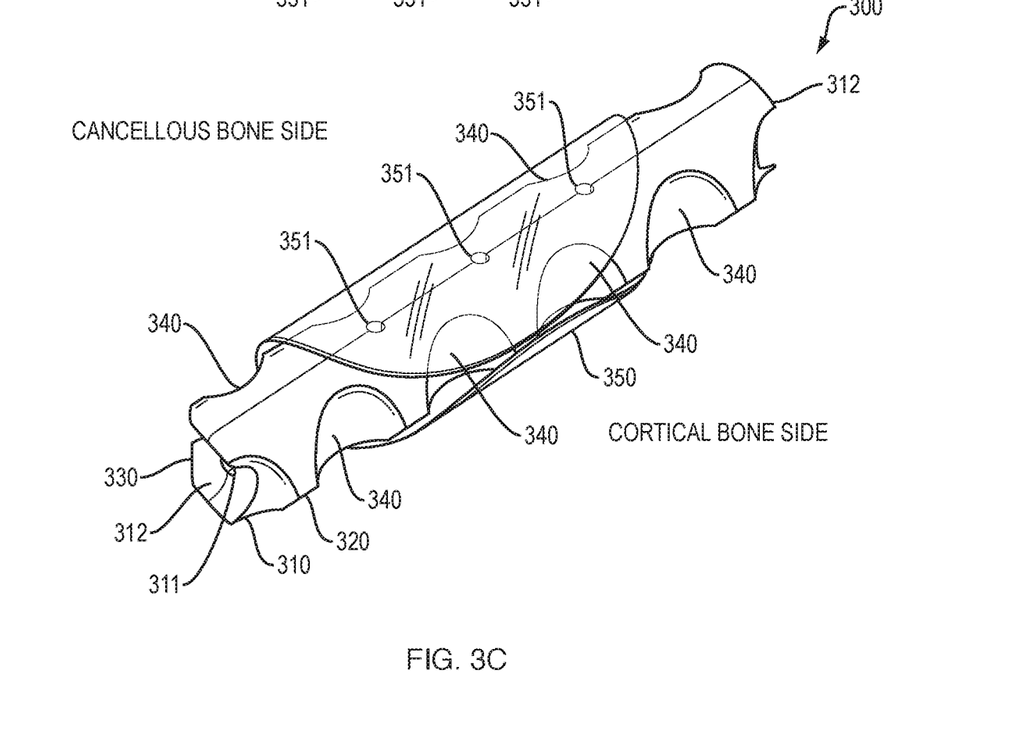

As shown in FIGS. 3A to 3C, some embodiments of the invention includes a bone graft implant 300. The bone graft implant 300 includes a body 310 having a generally circular section, but with scalloped or V-shaped reliefs 340 along the surfaces of the first portion 320 and second portion 330. Furthermore, the body 310 includes a cannula 311 that traverses the length of body 310 from end 312 to the other end 312. The ends 312 are configured to be concave as shown in FIGS. 3A and 3C. In some embodiments, the bone graft implant 300 may include a bioincorporable membrane or matrix 350 that may be affixed to the body 310 with membrane fixation elements 352 that are connected to the body 310 through radial holes 351. As shown in FIGS. 3A and 3B, the membrane fixation element 352 may be sutures.

In some embodiments, the invention includes a method for treating bone in a patient in need thereof, the method including providing, affixing, or otherwise introducing a bone graft implant described herein to a surface of the patient's bone and affixing the bone graft implant to said surface of the patient's bone. In some embodiments, the bone graft implant may be introduced through an introducing device or system, which may include an endoscopic device or devices. In some embodiments, a bone graft implant described herein may be introduced to a surface of the patient's bone through a surgical procedure. In some embodiments, the surgical procedures may include open surgery, laparoscopic surgery, endoscopic surgery, arthroscopic surgery, and the like. In some embodiments, the surgical procedures may include minimally invasive surgical procedures (e.g., MIS), which include, without limitation, laparoscopic surgical procedures, endoscopic surgical procedures, arthroscopic surgical procedures, and the like, that involve the use of a relatively small incision, as compared to open surgery, and an endoscope. In some embodiments, the bone graft implants described herein may be used in MIS approaches and therapies. In certain embodiments, the bone graft implants described herein may be used to treat lumbar facet joints, which result in lower back pain with mild stenosis. In certain embodiments, the bone graft implants described herein may be used to provide orthopaedic bone fusion. In some embodiments, the bone graft implants described herein may be used to fuse fractured bones in the spine, femur, tibia, humerus, ulna, radius, and/or bones of the extremities. In some embodiments, the bone graft implants may be used to fuse one or more vertebrae, one or more long bones, or one or more short bones, and the like.

In some embodiments, the invention may include a method for preparing a bone graft implant as described herein. The methods may include modifying the porosity of at least one of the first portion and second portion of the bone graft implant by demineralizing the first portion and/or the second portion of the bone graft implant.

In some embodiments, the invention may include a kit for treating bone or another related disease in a patient in need thereof. In some embodiments, the kit may include a bone graft implant, as described herein, and an introducing device configured to introduce the bone graft implant at a surface of the patient's bone.

The bone graft implants described herein may be positioned against cortical and/or cancellous bone. Furthermore, such implants may wick platelet rich fibrin gel, bone marrow, or bone marrow aspirate (BMA). Additionally, such grafts are conformable and may be molded to match bone tissue. In some embodiments, the bone graft implants may be delivered through an endoscope with MIS. Preparation of the materials described herein, including the bioincorporable membrane does not require centrifugation.

A number of patent and non-patent publications are cited herein in order to describe the state of the art to which this invention pertains. The entire disclosure of each of these publications is incorporated by reference herein.

While certain embodiments of the invention have been described and/or exemplified above, various other embodiments will be apparent to those skilled in the art from the foregoing disclosure. The invention is, therefore, not limited to the particular embodiments described and/or exemplified, but is capable of considerable variation and modification without departure from the scope and spirit of the appended claims.

Moreover, as used herein, the term "about" means that dimensions, sizes, formulations, parameters, shapes and other quantities and characteristics are not and need not be exact, but may be approximate and/or larger or smaller, as desired, reflecting tolerances, conversion factors, rounding off, measurement error and the like, and other factors known to those of skill in the art. In general, a dimension, size, formulation, parameter, shape or other quantity or characteristic is "about" or "approximate" whether or not expressly stated to be such. It is noted that embodiments of very different sizes, shapes and dimensions may employ the described arrangements.

Furthermore, the transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All implants, devices, kits, and methods described herein that embody the invention can, in alternate embodiments, be more specifically defined by any of the transitional terms "comprising," "consisting essentially of," and "consisting of."

What is claimed is:

1. A substantially cylindrical bone graft implant sized and configured for endoscopic introduction to a bone of a patient, the bone graft comprising:
    a first end, a second end, and a longitudinal axis extending from the first end to the second end;
    a cortical-bone-facing portion that is porous extending along a first side of the bone graft implant from the first end to the second end;
    a cancellous-bone-facing portion that is porous extending along a second side of the bone graft implant from the first end to the second end;
    one or more reliefs formed on at least one of the cortical-bone-facing portion and the cancellous-bone-facing portion, the one or more reliefs being configured to allow the bone graft implant to be flexed when the bone graft implant is being introduced to the bone of the patient, wherein the one or more reliefs are selected from the group consisting of U-shaped reliefs, scalloped reliefs, and V-shaped reliefs; and
    a cannula that axially traverses a length of the bone graft implant,
    wherein the cancellous-bone-facing portion of the bone graft implant is configured to be placed proximate to a surface of the bone of the patient,
    wherein the cortical-bone-facing portion comprises cortical bone, and
    wherein the cancellous-bone-facing portion comprises cancellous bone.

2. The bone graft implant of claim 1, wherein at least one of the cortical-bone-facing portion and cancellous-bone-facing portion comprises autograft bone.

3. The bone graft implant of claim 1, wherein at least one of the cortical-bone-facing portion and cancellous-bone-facing portion comprises allograft bone.

4. The bone graft implant of claim 1, wherein at least one of the cortical-bone-facing portion and cancellous-bone-facing portion comprises xenograft bone.

5. The bone graft implant of claim 1, wherein at least one of the cortical-bone-facing portion and cancellous-bone-facing portion comprises synthetic bone.

6. The bone graft implant of claim 1, wherein at least one of the cortical-bone-facing portion and the cancellous-bone-facing portion further comprises one or more of hyaluronic acid, B-TCP, ceramic, PLA, PLGA, and PLLA.

7. The bone graft implant of claim 1, wherein at least one of the cortical-bone-facing portion and the cancellous-bone-facing portion further comprises growth factors, platelet rich plasma, platelets, cells, peptides, or a combination thereof.

8. The bone graft implant of claim 1, wherein the bone graft implant has an outer diameter of about 3 mm to about 10 mm.

9. The bone graft implant of claim 1, wherein the bone graft implant has a length of about 20 mm to about 120 mm.

10. The bone graft implant of claim 1, wherein the bone graft implant is a composite.

11. The bone graft implant of claim 1, wherein the bone graft implant comprises a circular cross section.

12. The bone graft implant of claim 1, wherein the bone graft implant comprises a substantially flat surface.

13. The bone graft implant of claim 1, wherein at least one of the cortical-bone-facing portion and the cancellous-bone-facing portion comprises a convex portion, a concave portion, or a combination thereof.

14. The bone graft implant of claim 1, wherein at least one of the cortical-bone-facing portion and the cancellous-bone-facing portion comprise a channel.

15. The bone graft implant of claim 1, wherein at least one of the cortical-bone-facing portion and the cancellous-bone-facing portion is configured to buttress a bone, metal rod, or PEEK rod.

16. The bone graft implant of claim 1, wherein at least one of the cortical-bone-facing portion and cancellous-bone-facing portion comprise scalloped reliefs or V-shaped reliefs.

17. The bone graft implant of claim 1, wherein at least one of the cortical-bone-facing portion and cancellous-bone-facing portion comprises U-shaped reliefs.

18. The bone graft implant of claim 1, wherein bone graft implant is pre-hydrated.

19. The bone graft implant of claim 1, wherein the cortical-bone-facing portion is more porous than the cancellous-bone-facing portion.

20. The bone graft implant of claim 1, wherein the cancellous-bone-facing portion is more porous that the cortical-bone-facing portion.

21. The bone graft implant of claim 1, wherein the cortical-bone-facing portion and cancellous-bone-facing portion have about the same porosity.

22. The bone graft implant of claim 1, wherein the porosity of the cortical-bone-facing portion is uniform.

23. The bone graft implant of claim 1, wherein the porosity of the cortical-bone-facing portion is non-uniform.

24. The bone graft implant of claim 1, wherein the cortical-bone-facing portion comprises a porous gradient wherein a pore size at a surface of the cortical-bone-facing portion is greater than a pore size at an interior of the cortical-bone-facing portion.

25. The bone graft implant of claim 1, wherein the cortical-bone-facing portion comprises a porous gradient wherein a pore size at a surface of the cortical-bone-facing portion is less than a pore size at an interior of the cortical-bone-facing portion.

26. The bone graft implant of claim 1, wherein the cortical-bone-facing portion comprises a porous gradient wherein a pore size at a first surface of the cortical-bone-facing portion is greater than a pore size at a second surface of the cortical-bone-facing portion.

27. The bone graft implant of claim 26, wherein the pore sizes of the porous gradient vary lengthwise.

28. The bone graft implant of claim 1, wherein the porosity of the cancellous-bone-facing portion is uniform.

29. The bone graft implant of claim 1, wherein the porosity of the cancellous-bone-facing portion is non-uniform.

30. The bone graft implant of claim 1, wherein the cancellous-bone-facing portion comprises a porous gradient wherein a pore size at a surface of the cancellous-bone-facing portion is greater than a pore size at an interior of the cancellous-bone-facing portion.

31. The bone graft implant of claim 1, wherein the cancellous-bone-facing portion comprises a porous gradient wherein a pore size at a surface of the cancellous-bone-facing portion is less than a pore size at an interior of the cancellous-bone-facing portion.

32. The bone graft implant of claim 1, wherein the cancellous-bone-facing portion comprises a porous gradient wherein a pore size at a first surface of the cancellous-bone-facing portion is greater than a pore size at a second surface of the cancellous-bone-facing portion.

33. The bone graft implant of claim 32, wherein the pore sizes of the porous gradient vary lengthwise along the length of the cancellous-bone-facing portion.

34. The bone graft implant of claim 1, wherein the cannula is configured to allow the bone graft implant to be introduced to the bone of the patient on a guide wire or k-wire.

35. The bone graft implant of claim 1, comprising one or more securing holes that radially traverses a width of the bone graft implant.

36. The bone graft implant of claim 1, comprising a bioincorporable membrane disposed proximate to at least one of the cortical-bone-facing portion and the cancellous-bone-facing portion of the bone graft implant.

37. The bone graft implant of claim 36, wherein the bioincorporable membrane is secured to the bone graft implant by one or more membrane fixation elements.

38. The bone graft implant of claim 37, wherein the membrane fixation elements comprise sutures, screws, adhesive, or a combination thereof.

39. The bone graft implant of claim 36, wherein the bioincorporable membrane comprises a fibrin membrane.

40. The bone graft implant of claim 36, wherein the bioincorporable membrane comprises a platelet rich fibrin membrane.

41. The bone graft implant of claim 36, wherein the bioincorporable membrane comprises one or more of autograft amnion, autograft chorion, autograft dermis, autograft fascia, or a combination thereof.

42. The bone graft implant of claim 36, wherein the bioincorporable membrane comprises one or more of allograft amnion, allograft chorion, allograft dermis, allograft fascia, or a combination thereof.

43. The bone graft implant of claim 36, wherein the bioincorporable membrane comprises one or more of xenograft amnion, xenograft chorion, xenograft dermis, xenograft fascia, or a combination thereof.

44. The bone graft implant of claim 36, wherein the bioincorporable membrane consists of a platelet rich fibrin membrane.

45. The bone graft implant of claim 36, wherein the bioincorporable membrane is a platelet rich fibrin matrix.

46. The bone graft implant of claim 36, wherein the bioincorporable membrane comprises growth factors, platelet rich plasma, cells, peptides, or a combination thereof.

47. The bone graft implant of claim 1, wherein at least one of the cortical-bone-facing portion and the cancellous-bone-facing portion are configured to receive one or more bone fixation elements configured to affix the bone graft implant to the bone of the patient.

48. The bone graft implant of claim 47, wherein the bone fixation elements comprise sutures, screws, staples, adhesive, or a combination thereof.

49. The bone graft implant of claim 1, comprising a concave shape at the first end and/or the second end of the bone graft implant.

50. A kit for treating bone in a patient in need thereof, the kit comprising a bone graft implant according to claim 1, and an introducing device configured to introduce the bone graft implant at the surface of the bone of the patient.

51. The bone graft implant of claim 1, wherein the cancellous bone and/or the cortical bone is demineralized.

\* \* \* \* \*